United States Patent [19]

Russell et al.

[11] Patent Number: 5,683,383
[45] Date of Patent: Nov. 4, 1997

[54] INTERNAL RING RELEASE ERECTION DEVICE

[76] Inventors: John C. Russell, 19906 - 30th Ct. E., Sumner, Wash. 98390; Jack H. Philbrick, Jr., 902 A St. SE., Auburn, Wash. 98002

[21] Appl. No.: 511,792

[22] Filed: Aug. 7, 1995

[51] Int. Cl.⁶ ................................................ A61F 5/00
[52] U.S. Cl. .................................... 600/39; 600/41
[58] Field of Search .............................. 600/38–41

[56] References Cited

U.S. PATENT DOCUMENTS

| | | | |
|---|---|---|---|
| 4,753,227 | 6/1988 | Yanuck, Jr. | 600/41 |
| 5,125,890 | 6/1992 | Merrill et al. | 600/39 |
| 5,195,943 | 3/1993 | Chaney | 600/41 |
| 5,468,211 | 11/1995 | Weich | 600/39 |

*Primary Examiner*—John P. Lacyk
*Attorney, Agent, or Firm*—David L. Tingey

[57] ABSTRACT

An expanded elastic ring is supported in an annular groove within a ring outer cylinder for use in vacuum therapy of a dysfunctional penis. The cylinder has an open end for initial placement against a user's body with the penis contained within the cylinder. The cylinder further comprises a cap on a closed end into which a vacuum pump is integrated. The elastic ring expanded around an inner cylinder into an annular groove is remotely released within a vacuum drawn within the cylinder. In a first embodiment, the vacuum effects the release as the inner cylinder is withdrawn into an outer cylinder until the ring falls off of the inner cylinder end. In a second embodiment, push rods extending into the annular groove push the ring past a stationary inner cylinder, effected by rotation of the cap on the cylinder. An inclined face on the cap bottom surface engages the rod, pushing the rod into the annular groove.

10 Claims, 3 Drawing Sheets

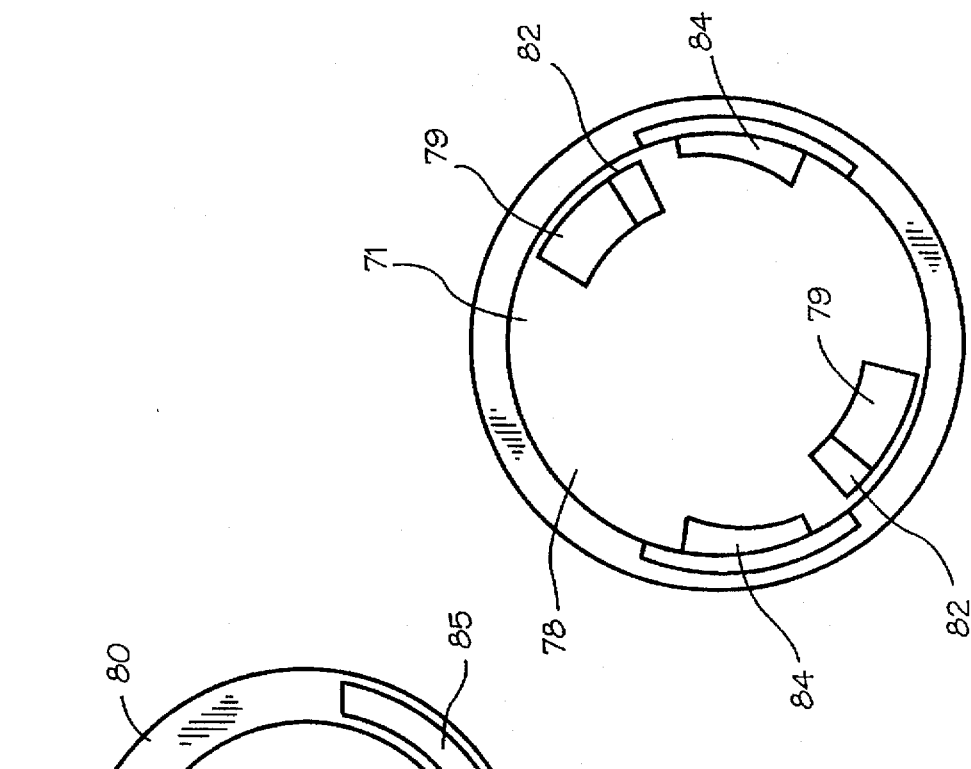
FIGURE 6
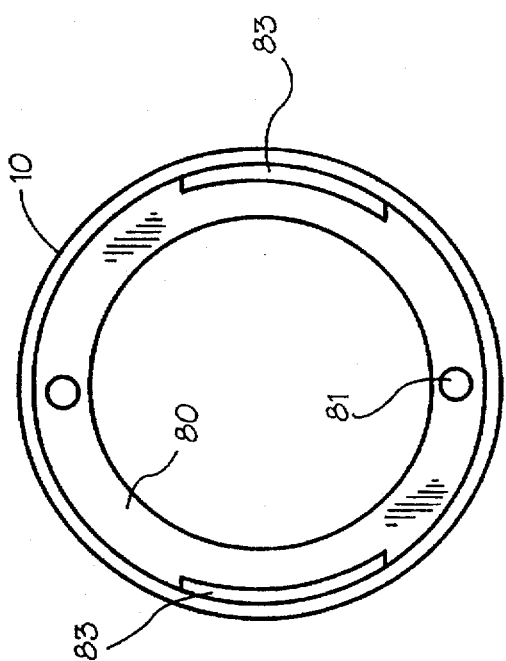
FIGURE 4
FIGURE 5

INTERNAL RING RELEASE ERECTION DEVICE

FIELD OF THE INVENTION

This invention relates to devices that artificially achieve an erection of a penis, and particularly to mechanical devices that cause a penile erection by creating a vacuum that causes blood to be pulled into the penis and releasing a constricting elastic about the base of the penis.

BACKGROUND

It is known in the art to have devices that produce - penile erection. Specifically, use of suction devices to produce penile tumescence in combination with constriction bands placed about the base of the penis to maintain an erection has been known for over 80 years. Such bands have been commercially available for almost 20 years.

Though other methods, such as injection and surgically implanted prostheses, are available for treatment of penile erectile dysfunction, the overwhelming choice presently is vacuum therapy with more than 100,000 prescriptions issued in 1993. By comparison, in the same period there were between 40,0000 and 50,000 new-patient penile injection prescriptions and only 20,000 penile implants.

Vacuum therapy employs a cylinder in which the flaccid penis is placed. The cylinder is held tight against the body while a pump attached to or integrally a part of the cylinder draws a vacuum in the cylinder around the penis typically ranging from 75 to 380 mm Hg. The user's blood is thus drawn into the penis in response to the vacuum and erection is achieved.

The problem then becomes retaining the blood in the penis, and hence the erection, when the cylinder is removed. Previously, an expanded elastic constriction ring was pushed over the end of the cylinder and off onto the base of the penis, preventing the blood from escaping as the ring contracted. The technique performed reasonably well but lost some effectiveness as blood would escape in the brief period between the time the cylinder was withdrawn from its seal against the body and the time the ring was slid to its required location at the base of the penis. It was not possible to maintain the seal of the cylinder together with the vacuum it maintained and still position the elastic ring to the needed position. Thus, a degree of the achieved erection was compromised.

SUMMARY OF THE INVENTION

The present vacuum therapy ring release system overcomes the deficiency of prior vacuum systems by supporting an expanded elastic ring within a vacuum cylinder into which a dysfunctional flaccid penis is placed with the cylinder open end pushed against a user's groin area to establish a vacuum seal. As with prior devices, a vacuum, or reduced air pressure, is drawn in the cylinder by means of a vacuum pump. However, unlike prior devices, the elastic ring is remotely released within the vacuum volume. Thus, the ring is in place around the penis and preventing blood escape before the vacuum seal of the cylinder and the body is broken.

The elastic ring can be supported within the vacuum cylinder and then remotely released by any of a large number of mechanisms. The import of the invention is not in the particular mechanism employed to achieved the internal ring release but in the recognition of the problem of external ring releases and the solution disclosed of supporting the ring internal to the vacuum cylinder and releasing it to close around the engorged penis within the vacuum before the vacuum is breached by removing the cylinder from the body.

One embodiment is to incorporate push rods extending in the cylinder from a cap on a cylinder closed end that pushes the ring out of a groove, the ring then collapsing around the base of a user's penis to constrict blood flow—all within the vacuum of the cylinder before the vacuum is broken by removing the cylinder from the user's groin area.

BRIEF DESCRIPTION OF THE DRAWINGS

FIG. 4 is a top view of the pump annulus.

FIG. 5 is a top view of the cylinder.

FIG. 6 is a bottom view of the pump.

DETAILED DESCRIPTION OF THE PREFERRED EMBODIMENT

Figure 1:
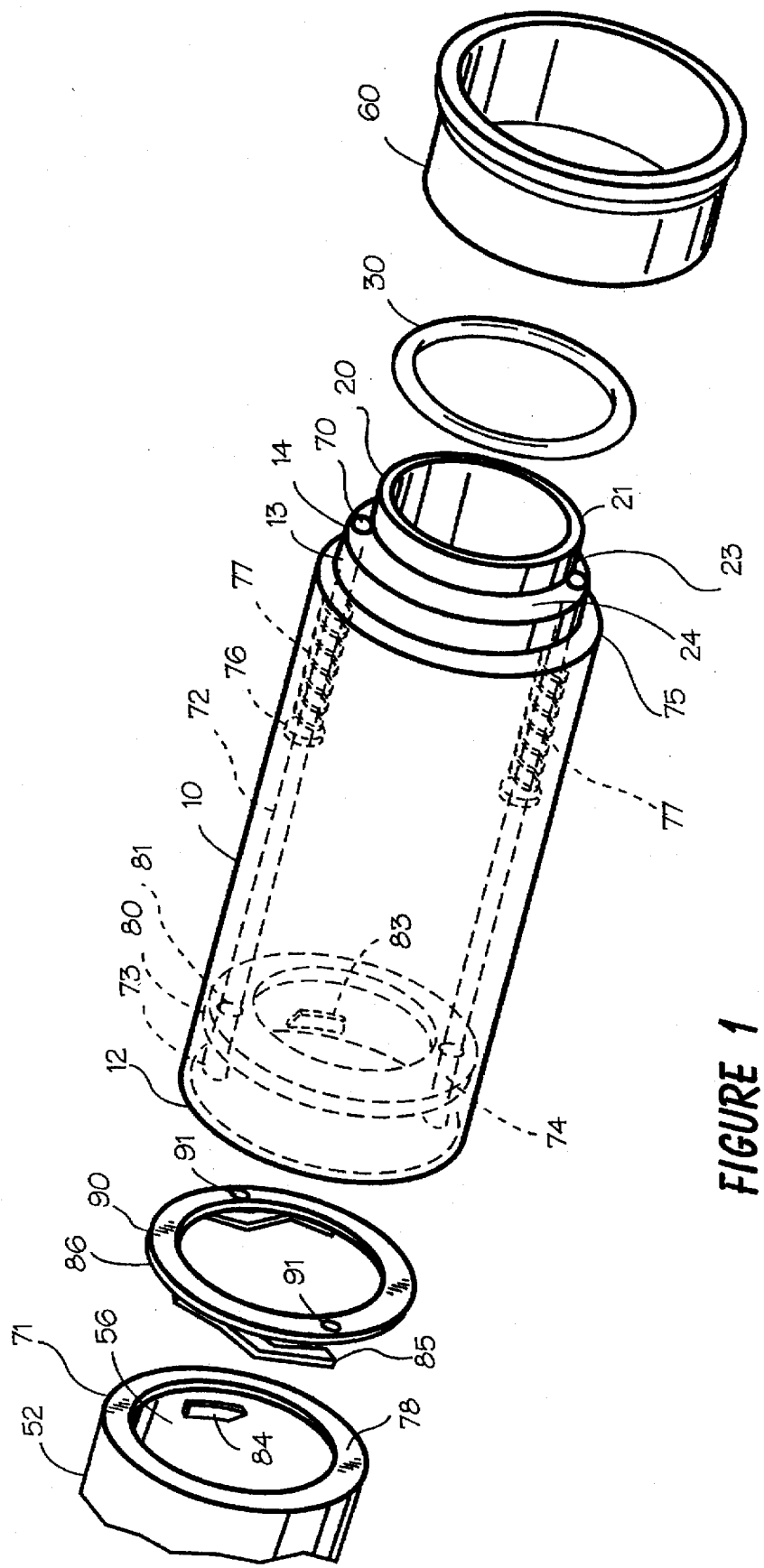
FIG. 1 is an exploded view of the ring release device.
Figure 2:
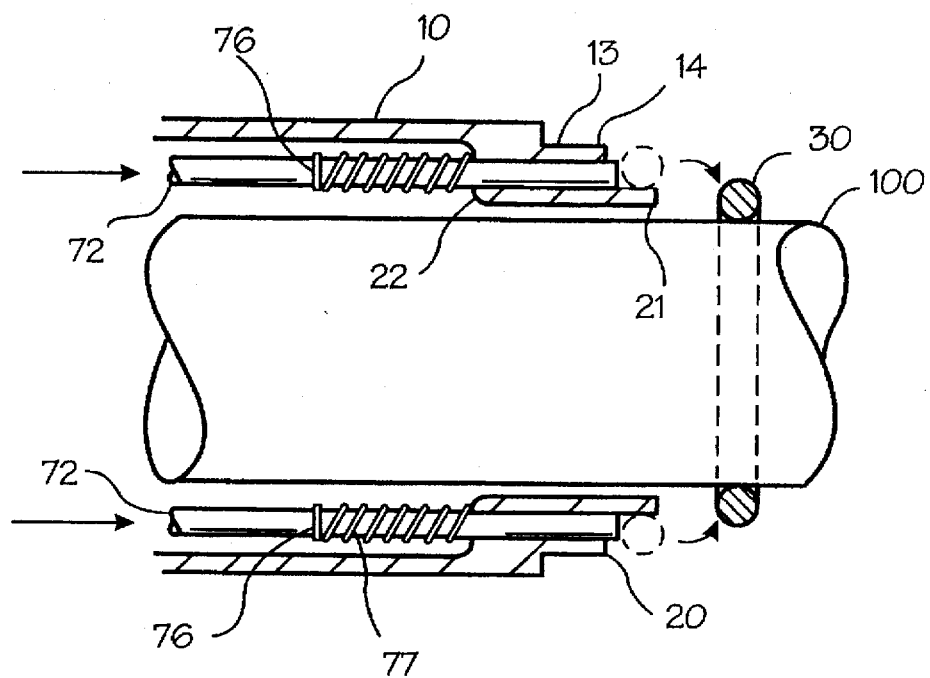
FIG. 2 shows internal release of an expanded elastic ring onto a penis.
Figure 3:
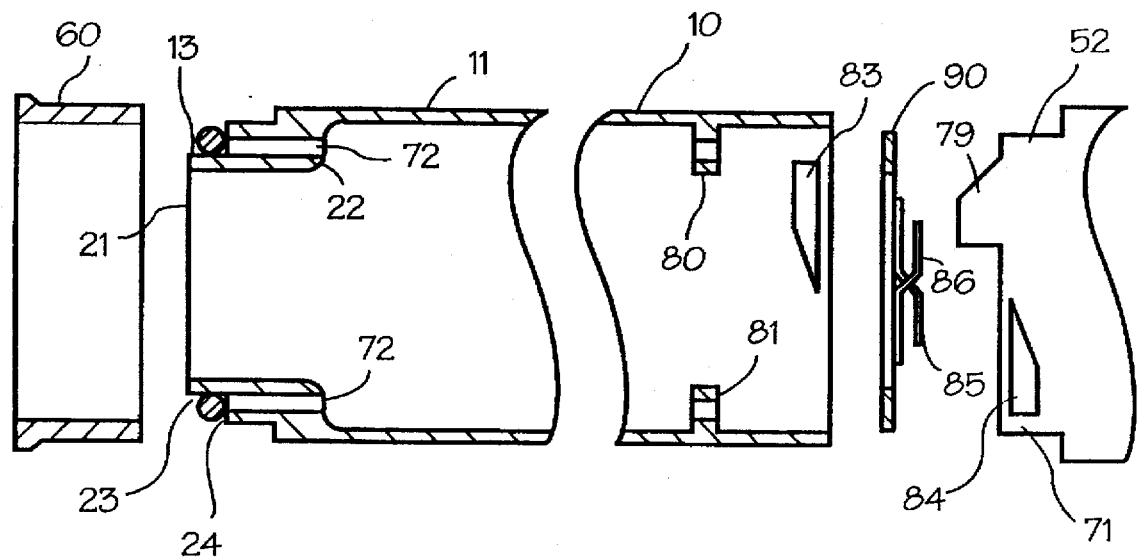
FIG. 3 is a cut-away view of the ring release device.

Referring to the figures, the internal ring release erection device 1 comprises a hollow outer cylinder 10 having a side wall 11, a closed end 12, and an open end 13. Integral with and internal the side wall 11 near the open end 13 but spaced apart a distance therefrom is a ring support ledge 14.

On the support ledge 14 is an inner cylinder 20 at the ring support ledge 14 internal to and concentric with the outer cylinder 10 terminating in first and second ends 21 and 22. The first end 21 extends past the ring support ledge 14 toward the outer cylinder open end 13 to form an annular groove 23 with a base 24 in the ring support ledge 14. An elastic ring 30 is then expanded around the inner cylinder 20 and placed in the annular groove 23.

The elastic constriction ring 30 within the vacuum volume of the outer cylinder 10 is released out of the annular groove 23 after a user's penis 100 is engorged, collapsing at the base of the penis 100, by moving the ring 30 relative to the inner cylinder 20 so the ring 30 falls off of the cylinder end 21. It is irrelevant whether the inner cylinder 20 is withdrawn from within a stationary ring 30 or the ring 30 is moved on a stationary inner cylinder 20

An inner cylinder 20 is affixed within the ring 30 support ledge 14 forming an annular groove 23 toward the outer ring open end 13 with a base 24 on the ring support ledge 14. The elastic constriction ring 30 is placed in the groove 23 preparatory to release under vacuum. For convenience in mounting the ring 30 in the groove 23, the cylinder may further include a tube section 60 from intermediate the support ledge to its open end removably engaged around the cylinder wall 11 intermediate the support ledge 14 comprising an outer side of the groove 23. Thus, when the tube section 60 is removed, the groove 23 presents a shelf on the extending cylindrical support wall 11. With the tube section 60 removed, an elastic ring 30 is then conveniently placed on the shelf, expanded around the inner cylinder 20. The tube section 60 is then replaced slideably over the cylinder wall 11, sized to fit snugly thereon, thereby establishing the elastic ring 30 in the annular groove 23 internal the cylinder.

To facilitate release of the ring 30 from the groove 23, the support ledge 14 has one or more bores 70 parallel to the cylinder wall 11 terminating at the groove base 24. At the cylinder closed end 12 is a rotatable cap 71 for closing the outer cylinder 10 and for causing the elastic ring 30 to be released from the annular groove 23. Integral with and internal the cylinder side wall 11 near the closed end 12 but spaced apart a distance therefrom is an inward-extending circumferential rim 80 having one or more holes 81 therethrough in alignment with the bore or bores 70 in the support ledge 14. A push rod 72 with a head 73 on a rod end 74 fits through each rim hole 81 and ledge bore 70, terminating with a second rod end 75 at the groove base 24 and extending in its rest position beyond the rim 80 toward the cylinder closed end 12. To support the push rod 72 in this rest position, the push rod 72 includes a stop 76 intermediate its length and a coil spring 77 through which the push rod 72 passes between the stop 76 and the ledge 14. Thus, in its rest position the rod 72 is supported by the spring 77. When the rod 72 is pushed downward against the spring 77 the rod 72 enters the annular groove 23 containing the elastic constriction ring 30, pushing the ring out of the groove 23. When the rod 72 is released, the spring 77 returns it to its rest position.

The internal movement of the rod 72 may be effected by any of a number of methods designed to urge the elastic ring 30 out of the annular groove 23 internal to the cylinder while under vacuum. In the preferred embodiment, the rotatable cap 71 having a flat undersurface 78 includes for each push rod 72 a protrusion 79 on its undersurface 78 that extends beyond the push rod head 73 toward the cylinder rim 80. A protrusion inclined face 82 ramps from the cap undersurface 78 and presents itself to the push rod 72 such that when the cap 71 is rotated, the inclined face 82 moves against the push rod head 73 urging the rod 72 downward away from the cap 71.

To lock the cap 71 in the cylinder 10 as it is being rotated, a latching mechanism between the cylinder and the cap 71 may be provided, such as one or more holds 83 on the outer cylinder wall 11 matching a corresponding catch 84 for each hold 83 arranged on the cap undersurface 78 such that the catch 84 extends into the cylinder 10 past the hold 83 and then snugly under the hold 83 as the cap 71 is rotated, thereby securing the cap 71 onto the cylinder 10 with each cap protrusion 79 presenting its inclined face 82 to a corresponding push rod 72. As the cap 71 is further rotated, the catch 84 continues under the hold as the inclined face 82 urges the push rod 72 down.

To ease the interface of the cap protrusion inclined face 82 with the push rod head 73, a flexible rim ramp 85, perhaps constructed of spring steel or similar flexible material with spring bias, is attached to the rim 80 with its distal end 88 over the push rod head 73 and with an inclined surface 86 disposed opposite the cap protrusion inclined face 82. Thus, when the inclined face 82 rotates toward the push rod 72, the rim ramp 85 intercepts the inclined face 82, and the ramp distal end 86 is urged down onto the push rod head 73 moving the push rod 72 down into the annular groove 23.

An annulus 90 may also be provided between the cylinder rim 80 and the cap 71 on which is mounted the flexible rim ramp 85. The annulus 90 has holes 91 matching the rim holes 81 through with the push rod 72 passes and holds the annulus 90 in position with each rim ramp 85 over the corresponding push rod head 73.

An air pump 50, required to draw a mild vacuum within the cylinder when the cylinder open end 13 is sealed against a user, may be provided in a number of embodiments. For example, a hole for attachment of an air tube may be provided in the cylinder, the air tube then running to and providing fluid communication with a remote air pump. However, in this instance, because anticipated use demands a manual pump operated with one hand, it is convenient to integrate the air pump 50 with the cylinder, held in place by a user's other hand. Thus, the preferred embodiment includes a cylinder cap 71 comprising the air pump 50, although any means for reducing the air pressure within the outer cylinder 10 is applicable and deemed to be a part of this invention in combination with the other elements described.

The air pump 50 (details not shown) comprises an air pump cylinder with a plunger slideably fitted therein typically with an O-ring around the plunger making an air seal with the pump cylinder. The cap 71 is provided with a cap hole allowing fluid communication with the ring outer cylinder 10. A vacuum pneumatic valve is sealed in the cap hole which closes under pressure such as when the plunger moves into the pump cylinder and opens under vacuum such as when the plunger moves away from the valve. Similarly, a release pneumatic valve is placed in the pump cylinder with reverse function. That is, the release valve allows air to exhaust from the pump cylinder when the plunger moves toward the closed vacuum pneumatic valve but closes when the plunger reverses direction. A handle extending out of the pump cylinder is typically provided on the plunger for convenience in operating the plunger in the pump cylinder.

Having described the invention, what is claimed is:

1. An internal ring release erection device comprising a hollow outer cylinder having a side wall, a closed end, and an open end adapted to achieve a temporary seal against a user's body, a ring support ledge integral with and internal the side wall near the open end but spaced apart a distance therefrom, a releasable ring, an inner cylinder at the ring support ledge internal to and concentric with the outer cylinder terminating in first and second ends with the first end extending past the ring support ledge toward the outer cylinder open end forming an annular groove with a base in the ring support ledge, the elastic ring received therein expanded around the inner cylinder, means for reducing air pressure within the outer cylinder when its open end achieves a temporary seal against a user's body, means for releasing the elastic ring from the annular groove internal the outer cylinder while said outer cylinder open end maintains said temporary seal against said user's body with reduced air pressure within the outer cylinder comprising means for moving the elastic ring longitudinally relative to the inner cylinder which includes a. an inner cylinder affixed within the ring support ledge, and b. means for urging the elastic ring out of the annular groove past the inner cylinder first end, causing the ring to release over the inner cylinder, including i. one or more push rods each with a head on a rim end, ii. the ledge with one or more ledge bores and one or more push rods slideably passing through one or more ledge bores terminating with a push rod groove end at the groove base, iii. means for remotely pushing said one or more push rods into the annular groove against the elastic ring.

2. The device of claim 4 in which the means for remotely pushing said one or more push rods into the annular groove comprises an inward-extending circumferential rim having one or more holes therethrough in alignment with said one or more ledge bores in the support ledge integral with and internal said outer cylinder side wall near the closed end but spaced apart a distance therefrom, said push rod having a length such that in a first, or rest, position it extends in said rest position beyond the rim toward the outer cylinder closed end, a stop intermediate the push rod length, a coil spring through which the push rod passes between the stop and the ledge to support the push rod in said rest position such that when the rod is pushed downward against the spring the rod enters the annular groove, pushing the ring out of the groove, and when the rod is released, the spring returns it to its rest position, a rotatable cap, means to secure the cap to the outer cylinder closing the outer cylinder closed end, means on the rotatable cap for remotely pushing the push rod into the annular groove.

3. The device of claim 2 in which the means on the rotatable cap for remotely pushing said push rod into the annular groove comprises a bottom surface on the rotatable cap including for each push rod a protrusion that extends beyond the push rod head toward the outer cylinder rim, a protrusion inclined face ramping away from the cap bottom surface and presenting itself to the push rod such that when the cap is rotated, the inclined face moves against the push rod head urging the rod downward away from the cap.

4. The device of claim 2 in which the means to rotatably secure the cap to the outer cylinder comprises one or more holds on the outer cylinder wall, a corresponding catch matching each hold and arranged on the cap bottom surface such that the catch extends into the outer cylinder past the hold and then snugly under the hold as the cap is rotated, thereby securing the cap onto the outer cylinder with each cap protrusion presenting its inclined face to a corresponding push rod in a first position, the catch having a length such that as the cap is further rotated to a second position, the catch continues under the hold as the inclined face urges the push rod down.

5. The device of claim 4 further comprising a flexible rim ramp connected to the rim at one end and with a distal end extending over a push rod and having a spring bias, the rim ramp disposed opposite the cap protrusion inclined face on the rim to present an interface of the cap protrusion inclined face with the push rod head such that when the inclined face rotates toward the push rod, the rim ramp intercepts the inclined face and the ramp distal end is urged down onto the push rod head moving the push rod down into the annular groove.

6. The device of claim 2 further comprising an annulus between the outer cylinder rim and the cap having holes matching the rim holes through which the push rod passes, a flexible rim ramp connected to the annulus at one end and with a distal end extending over a push rod and having a spring bias, the rim ramp disposed opposite the cap protrusion inclined face on the rim to present an interface of the cap protrusion inclined face with the push rod head such that when the inclined face rotates toward the push rod, the rim ramp intercepts the inclined face and the ramp distal end is urged down onto the push rod head moving the push rod down into the annular groove.

7. The device of claim 1 in which the means for reducing air pressure within the outer cylinder when its open end is sealed against a user's body comprises an air pump integrated with the outer cylinder operable with a user's hand holding the outer cylinder against his body and a second hand on the air pump, the improvement comprising, a cylinder cap integral with the air pump.

8. The device of claim 1 in which the outer cylinder from intermediate the support ledge to its open end comprises a tube section for convenience in mounting the ring in the groove removably engaged to the outer cylinder intermediate the support ledge and sized to fit snugly thereon, defining therein an outer side of the groove, such that when the tube section is removed, the groove presents a cylindrical shelf.

9. The method of causing a penile erection of a dysfunctional penis through vacuum therapy using an elastic ring to constrain blood artificially drawn into the penis using an outer cylinder having a closed end and an open end adapted to achieve a temporary seal against a user's body, and an elastic ring supported in an annular groove defined between an inner cylinder and the outer cylinder, said ring releasable within the outer cylinder around the penis while a vacuum is maintained in the outer cylinder and before the outer cylinder is separated from a user's body, the method comprising the following steps:

a. Installing an expanded elastic ring internal to the outer cylinder in the annular groove by
 i. Using an outer cylinder comprising a tube section removably engaged on the outer cylinder open end sized to fit snugly thereon and comprising therein an outer side of the groove, removing the tube section from the outer cylinder wall, the groove presenting therein a cylindrical shelf;
 ii. Placing an elastic ring on the shelf, expanded around the cylindrical shelf;
 iii. Replacing the tube section over the outer cylinder wall, thereby establishing the elastic ring in the annular groove internal the outer cylinder.

b. Inserting the penis into the open end of the inner cylinder;

c. Holding the outer cylinder open end tightly against the user's body to achieve a temporary seal;

d. Reducing air pressure within the outer cylinder until a penal erection is achieved;

e. While maintaining reduced air pressure, remotely releasing the elastic ring from the inner cylinder into the outer cylinder near its open end with the ring constricting around the penis;

f. Separating the outer cylinder from the user's body and penis.

10. The method of claim 9 in which the step of remotely releasing the elastic ring into the outer cylinder near its open end and around the penis preventing blood from escaping the penis while maintaining reduced air pressure further comprises the following steps:

a. Using an outer cylinder with a cap rotatably secured to the outer cylinder thereby closing the outer cylinder closed end by means of one or more holds on the outer cylinder wall, a corresponding catch matching each hold and arranged on the cap bottom surface such that the catch extends into the outer cylinder past the hold and then snugly under the hold as the cap is rotated, thereby securing the cap onto the outer cylinder, and one or more push rods each with a head on a rim end slideably secured within the outer cylinder and terminating with a push rod groove end at a groove in which the expanded elastic ring is supported, further comprising on the rotatable cap a bottom surface including for each push rod a protrusion on its undersurface with a bottom surface that extends beyond the push rod head toward the outer cylinder rim, a protrusion inclined face ramping from the cap bottom surface to the protrusion bottom surface and presenting itself to the push rod, rotating the cap to cause the inclined face to move against the push rod head urging the rod downward away from the cap, thereby remotely releasing the elastic ring from the annular groove internal the support cylinder while the outer cylinder open end maintains a temporary seal against a user's body.

* * * * *